US010349897B2

(12) United States Patent
Kobayashi et al.

(10) Patent No.: US 10,349,897 B2
(45) Date of Patent: Jul. 16, 2019

(54) BIOLOGICAL SIGNAL MEASURING SYSTEM

(71) Applicant: NIHON KOHDEN CORPORATION, Tokyo (JP)

(72) Inventors: Naoki Kobayashi, Tokyo (JP); Teiji Ukawa, Tokyo (JP); Kazumasa Ito, Tokyo (JP); Masahiro Takeuchi, Tokyo (JP); Yoshinori Ueda, Tokyo (JP); Hiroko Hagiwara, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 651 days.

(21) Appl. No.: 14/557,806

(22) Filed: Dec. 2, 2014

(65) Prior Publication Data

US 2015/0150513 A1    Jun. 4, 2015

(30) Foreign Application Priority Data

Dec. 4, 2013    (JP) ................................ 2013-251445

(51) Int. Cl.
*A61B 5/1455*    (2006.01)
*A61B 5/0205*    (2006.01)
(Continued)

(52) U.S. Cl.
CPC .......... *A61B 5/7246* (2013.01); *A61B 5/0205* (2013.01); *A61B 5/02416* (2013.01);
(Continued)

(58) Field of Classification Search
CPC ............ A61B 5/14551; A61B 5/02416; A61B 5/14552; A61B 5/7207; A61B 5/4818
See application file for complete search history.

(56) References Cited

U.S. PATENT DOCUMENTS 6,178,343 B1 *    1/2001    Bindszus ............. A61B 5/0245
                                                                          600/323
6,334,065 B1    12/2001    Al-Ali et al.
(Continued)

FOREIGN PATENT DOCUMENTS

CN           103501694 A      1/2014
JP           2002-516689 A    6/2002
(Continued)

OTHER PUBLICATIONS

The extended European Search Report for the related European Patent Application No. 14196031.0 dated May 26, 2015.
(Continued)

*Primary Examiner* — Eric F Winakur
(74) *Attorney, Agent, or Firm* — Pearne & Gordon LLP

(57) ABSTRACT

A biological signal measuring system includes: first and second optical sensors attached to first and second body portions of a subject; a first average oxygen saturation acquiring section acquiring a first average value corresponding to an average value of the first oxygen saturation corresponding to an arterial oxygen saturation in the first body portion in a predetermined time period starting at a first time; a second average oxygen saturation acquiring section acquiring a second average value corresponding to an average value of the second oxygen saturation corresponding to an arterial oxygen saturation in the second body portion in the predetermined time period starting at a second time that is different from the first time; and a difference value acquiring section acquiring a difference value, to be displayed, between the first average value and the second average value.

9 Claims, 5 Drawing Sheets

(51) Int. Cl.
*A61B 5/00* (2006.01)
*A61B 5/024* (2006.01)

(52) U.S. Cl.
CPC ...... *A61B 5/14551* (2013.01); *A61B 5/14552* (2013.01); *A61B 5/7203* (2013.01); *A61B 5/7278* (2013.01); *A61B 5/7282* (2013.01); *A61B 5/742* (2013.01); *A61B 5/746* (2013.01); *A61B 5/02427* (2013.01); *A61B 5/6826* (2013.01); *A61B 5/6829* (2013.01); *A61B 2503/04* (2013.01)

(56) References Cited

U.S. PATENT DOCUMENTS

| | | | | |
|---|---|---|---|---|
| 7,376,452 | B2 * | 5/2008 | Kobayashi | A61B 5/0059 600/322 |
| 2002/0082488 | A1 | 6/2002 | Al-Ali et al. | |
| 2003/0236452 | A1 * | 12/2003 | Melker | A61B 5/0873 600/323 |
| 2004/0059209 | A1 | 3/2004 | Al-Ali et al. | |
| 2005/0197551 | A1 | 9/2005 | Al-Ali et al. | |
| 2006/0173258 | A1 | 8/2006 | Kobayashi et al. | |
| 2006/0258923 | A1 | 11/2006 | Al-Ali et al. | |
| 2006/0258924 | A1 | 11/2006 | Al-Ali et al. | |
| 2006/0258925 | A1 | 11/2006 | Al-Ali et al. | |
| 2006/0270920 | A1 | 11/2006 | Al-Ali et al. | |
| 2006/0281983 | A1 | 12/2006 | Al-Ali et al. | |
| 2008/0071155 | A1 * | 3/2008 | Kiani | A61B 5/02416 600/324 |
| 2013/0197330 | A1 | 8/2013 | Al-Ali et al. | |
| 2013/0338519 | A1 * | 12/2013 | Chen | A61B 5/0452 600/521 |
| 2015/0018650 | A1 | 1/2015 | Al-Ali et al. | |

FOREIGN PATENT DOCUMENTS

| | | |
|---|---|---|
| JP | 2003-225214 A | 8/2003 |
| JP | 2006-231012 A | 9/2006 |
| JP | 4704037 B2 | 6/2011 |
| WO | 2004/000114 A1 | 12/2003 |

OTHER PUBLICATIONS

P D MacDonald et al.; "Simultaneous measurement of preductal and postductal oxygen saturation by pulse in oximetry in hyaline membrane disease."; Archives of Disease in Childhood 1992; 67: pp. 1166-1168.

P. Meier-Stauss et al.; "Pulse oximetry used for documenting oxygen saturation and right-to left shunting immediately after birth"; European Journal of Pediatrics 1990; 149; pp. 851-855.

European Office Action for Application No. 14 196 031.0 dated May 10, 2016.

Office Action issued in Patent Application No. JP-2013-251445 dated Jan. 24, 2017.

Chinese Office action issued in Patent Application No. CN-201410734721 dated Jul. 12, 2018.

Japanese Office Action issued in Patent Application No. 2013-251445 dated Aug. 23, 2017.

* cited by examiner

BIOLOGICAL SIGNAL MEASURING SYSTEM

CROSS-REFERENCE TO RELATED APPLICATION(S)

This application is based upon and claims the benefit of priority from prior Japanese patent application No. 2013-251445, filed on Dec. 12, 2013, the entire contents of which are incorporated herein by reference.

BACKGROUND

The presently disclosed subject matter relates to a biological signal measuring system which is used in congenital heart disease screening in neonates.

In order to perform congenital heart disease screening, a probe of a first pulse oximeter is attached to a first body portion (for example, the fingertip of the hand) of the subject, and that of a second pulse oximeter is attached to a second body portion (for example, the fingertip of the foot) of the subject (for example, see Patent Literature 1). In the case where the subject has congenital heart disease, a difference occurs between the values of arterial oxygen saturations (SpO2) which are detected in the first and second body portions. When the values of arterial oxygen saturations which are detected by the two pulse oximeters are compared to each other, therefore, presence or absence of congenital heart disease can be determined (for example, see Non-Patent Literatures 1 and 2).

(Patent Literature 1) Japanese Patent No. 4,704,037

(Non-patent Literature 1) P D Mcdonald, V Y Yu (1992), Simultaneous measurement of preductal and postductal oxygen saturation by pulse oximetry in hyaline membrane disease, Arch Dis Child 67: 1166-1168

(Non-patent Literature 2) P. Meier-Stauss, H. U. Bucher, R. Hurlimann, V. Konig, and R. Huch (1989), Pulse oximetry used for documenting oxygen saturation and right-to-left shunting immediately after birth, Eur J Pediatr 149: 851-855

The value of arterial oxygen saturation varies every moment. It is difficult for the medical person to visually compare numerical values displayed on two pulse oximeters at certain timing, and correctly identify the difference between the numerical values.

SUMMARY

The presently disclosed subject matter may provide a technique for reducing the burden of a medical person in, for example, congenital heart disease screening, and supporting correct determination.

According to the presently disclosed subject matter, there may be provided a biological signal measuring system comprising: a first optical sensor which is to be attached to a first body portion of a subject; a first attenuation ratio acquiring section which is configured to acquire a temporal change of a first attenuation ratio corresponding to an attenuation ratio of a plurality of wavelengths in the first body portion, based on a first signal output from the first optical sensor; a first oxygen saturation acquiring section which is configured to acquire a temporal change of a first oxygen saturation corresponding to an arterial oxygen saturation in the first body portion, based on the temporal change of the first attenuation ratio; a second optical sensor which is to be attached to a second body portion of the subject; a second attenuation ratio acquiring section which is configured to acquire a temporal change of a second attenuation ratio corresponding to an attenuation ratio of a plurality of wavelengths in the second body portion, based on a second signal output from the second optical sensor; a second oxygen saturation acquiring section which is configured to acquire a temporal change of a second oxygen saturation corresponding to an arterial oxygen saturation in the second body portion, based on the temporal change of the second attenuation ratio; a first average oxygen saturation acquiring section which is configured to acquire a first average value corresponding to an average value of the first oxygen saturation in a predetermined time period starting at a first time; a second average oxygen saturation acquiring section which is configured to acquire a second average value corresponding to an average value of the second oxygen saturation in the predetermined time period starting at a second time that is different from the first time; a difference value acquiring section which is configured to acquire a difference value between the first average value and the second average value; and a difference value displaying section which is configured to display the difference value.

The biological signal measuring system may further comprise: a cross-correlation function acquiring section which is configured to acquire a cross-correlation function of the temporal change of the first attenuation ratio and the temporal change of the second attenuation ratio, or a cross-correlation function of the temporal change of the first oxygen saturation and the temporal change of the second oxygen saturation, and the first time and the second time may be determined based on the cross-correlation function.

The biological signal measuring system may further comprise: a notifying section which, when the difference value is equal to or larger than a threshold, is configured to take a given notifying state.

When the first average value is smaller than a threshold, or when the second average value is smaller than the threshold, the notifying section may be configured to take the given notifying state irrespective of the difference value.

The biological signal measuring system may further comprise: a first average value displaying section which is configured to display the first average value; and a second average value displaying section which is configured to display the second average value.

The biological signal measuring system may further comprise: a first notifying section which, when the first average value is smaller than a threshold, is configured to take a given notifying state; a second notifying section which, when the second average value is smaller than a threshold, is configured to take a given notifying state; and a third notifying section which, when the difference value is equal to or larger than a threshold, is configured to take a given notifying state.

The biological signal measuring system may further comprise: a heart rate acquiring section which is configured to acquire a heart rate of the subject based on at least one of the first signal and the second signal; and a single heart rate displaying section which is configured to display the heart rate.

The heart rate acquiring section may be configured to select one of the first signal and the second signal which contains a smaller amount of noises, and acquire the heart rate based on the selected one of the first signal and the second signal.

The heart rate acquiring section may be configured to acquire, as the heart rate, an average value of: the heart rate based on the first signal; and the heart rate based on the second signal.

DETAILED DESCRIPTION OF EXEMPLARY EMBODIMENTS

Figure 1:
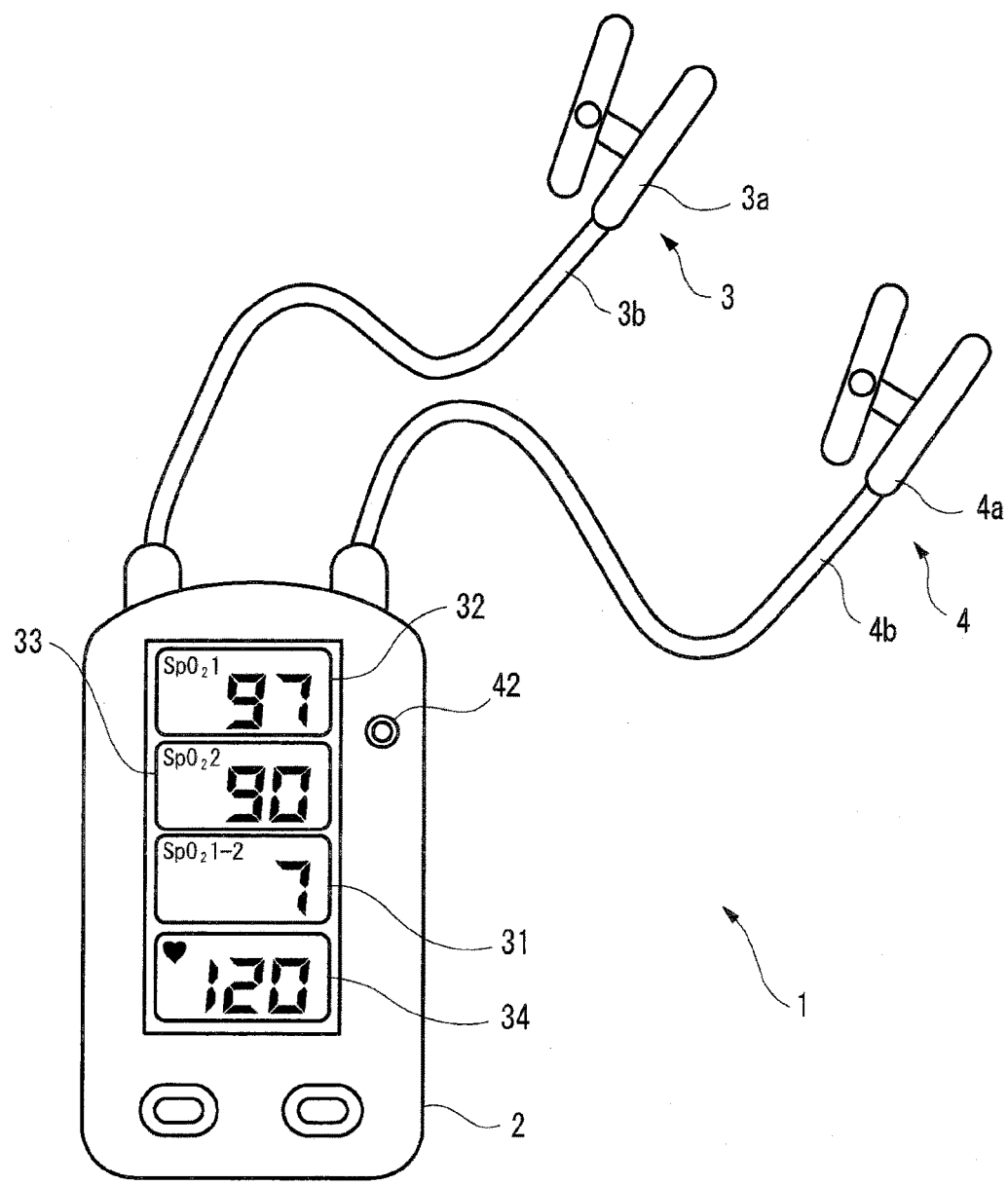
FIG. 1 is a view showing a biological signal measuring system of a first embodiment of the presently disclosed subject matter.

Embodiments of the presently disclosed subject matter will be described in detail with reference to the accompanying drawings. In the drawings which will be used in the following description, the scale is adequately changed in order to draw components in a recognizable size.

FIG. 1 shows a biological signal measuring system 1 of a first embodiment of the presently disclosed subject matter. The biological signal measuring system 1 includes a biological signal measuring apparatus 2, a first optical sensor 3, and a second optical sensor 4. The biological signal measuring apparatus 2 is a so-called pulse oximeter, and the first optical sensor 3 and the second optical sensor 4 function as probes of the pulse oximeter.

The first optical sensor 3 includes a fastening portion 3a and a cable 3b. The fastening portion 3a is to be attached to a first body portion (for example, the fingertip of the hand) of the subject. The fastening portion 3a includes a light emitter and a light receiver. The light emitter emits a red light beam and an infrared light beam. The light receiver outputs a first signal corresponding to the intensities of the red and infrared light beams which are transmitted through or reflected from the first body portion. The first signal is input to the biological signal measuring apparatus 2 through the cable 3b.

The second optical sensor 4 includes a fastening portion 4a and a cable 4b. The fastening portion 4a is to be attached to a second body portion (for example, the fingertip of the foot) of the subject. The fastening portion 4a includes a light emitter and a light receiver. The light emitter emits a red light beam and an infrared light beam. The light receiver outputs a second signal corresponding to the intensities of the red and infrared light beams which are transmitted through or reflected from the second body portion. The second signal is input to the biological signal measuring apparatus 2 through the cable 4b.

Figure 2:
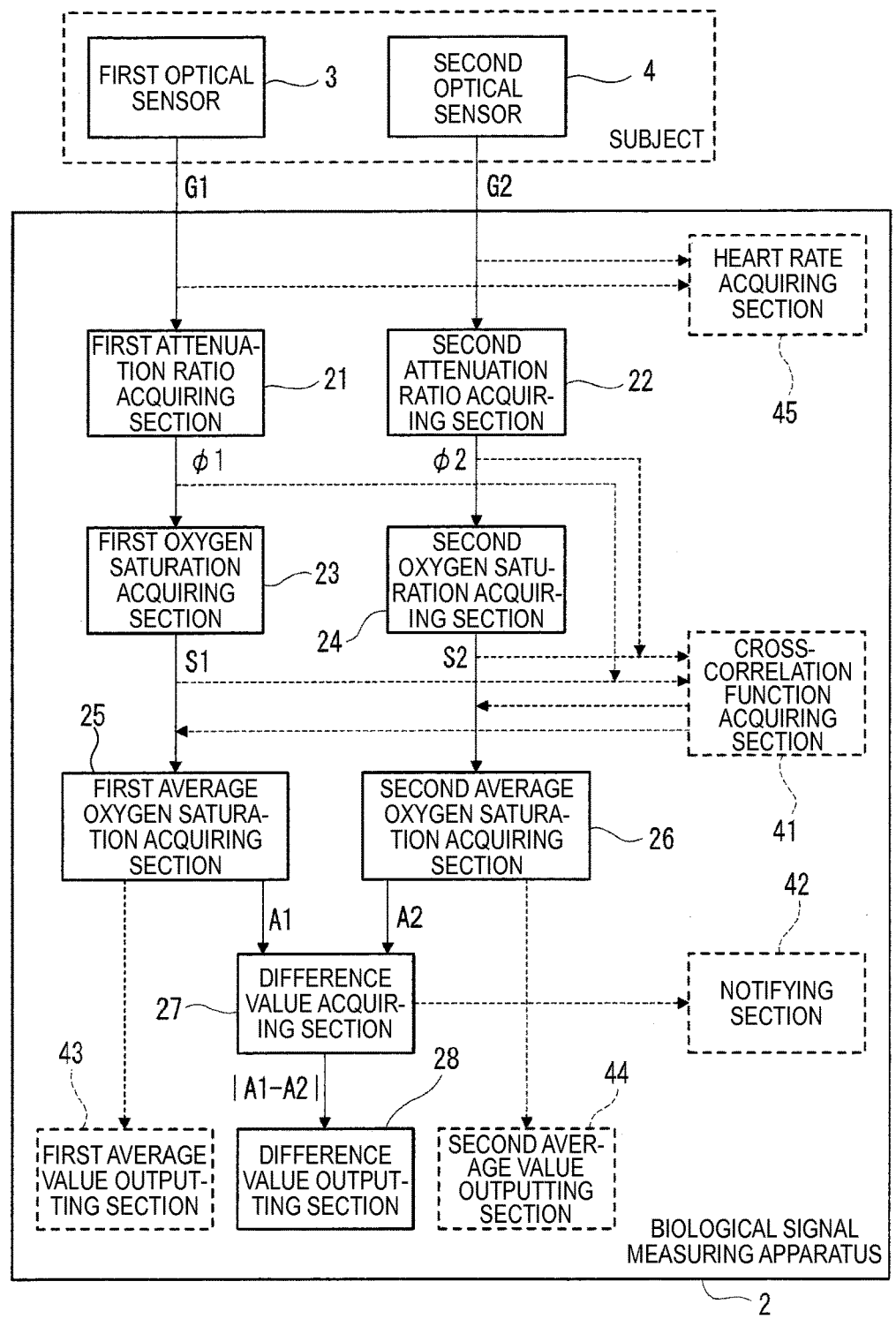
FIG. 2 is a functional block diagram showing the configuration of a biological signal measuring apparatus of the biological signal measuring system of FIG. 1.

FIG. 2 is a functional block diagram showing the configuration of the biological signal measuring apparatus 2. The biological signal measuring apparatus 2 includes a first attenuation ratio acquiring section 21, a second attenuation ratio acquiring section 22, a first oxygen saturation acquiring section 23, a second oxygen saturation acquiring section 24, a first average oxygen saturation acquiring section 25, a second average oxygen saturation acquiring section 26, a difference value acquiring section 27, and a difference value outputting section 28.

The first attenuation ratio acquiring section 21 acquires a temporal change of a first attenuation ratio $\phi 1$ corresponding to an attenuation ratio in the first body portion, based on the first signal G1 output from the first optical sensor 3. Specifically, attenuations of the red and infrared light beams due to transmission or reflection in the first body portion are acquired, and the ratio of the attenuations is set as the first attenuation ratio $\phi 1$. The first attenuation ratio $\phi 1$ is temporally changed in accordance with the blood pulsation in the first body portion.

The second attenuation ratio acquiring section 22 acquires a temporal change of a second attenuation ratio $\phi 2$ corresponding to an attenuation ratio in the second body portion, based on the second signal G2 output from the second optical sensor 4. Specifically, attenuations of the red and infrared light beams due to transmission or reflection in the second body portion are acquired, and the ratio of the attenuations is set as the second attenuation ratio $\phi 2$. The second attenuation ratio $\phi 2$ is temporally changed in accordance with blood pulsation in the second body portion.

The first oxygen saturation acquiring section 23 acquires a first oxygen saturation S1 corresponding to the arterial oxygen saturation in the first body portion, based on the first attenuation ratio $\phi 1$ acquired by the first attenuation ratio acquiring section 21. The method of calculating an arterial oxygen saturation from an attenuation ratio may be a related-art method. Therefore, description of the method is omitted. In accordance with the temporal change of the first attenuation ratio $\phi 1$, also the first oxygen saturation S1 is temporally changed.

The second oxygen saturation acquiring section 24 acquires a second oxygen saturation S2 corresponding to the arterial oxygen saturation in the second body portion, based on the second attenuation ratio $\phi 2$ acquired by the second attenuation ratio acquiring section 22. The method of calculating an arterial oxygen saturation from an attenuation ratio may be a related-art method. Therefore, description of the method is omitted. In accordance with the temporal change of the second attenuation ratio $\phi 2$, also the second oxygen saturation S2 is temporally changed.

The first average oxygen saturation acquiring section 25 acquires a first average value A1 corresponding to an average value of the first oxygen saturation S1 in a predetermined time period starting at a first time. The second average oxygen saturation acquiring section 26 acquires a second average value A2 corresponding to an average value of the second oxygen saturation S2 in a predetermined time period starting at a second time that is different from the first time. The difference value acquiring section 27 acquires the difference value |A1−A2| between the first average value A1 and the second average value A2. The reason for the processes of the first average oxygen saturation acquiring section 25, the second average oxygen saturation acquiring section 26, and the difference value acquiring section 27 will be described with reference to FIGS. 3A and 3B.

Figure 3A:
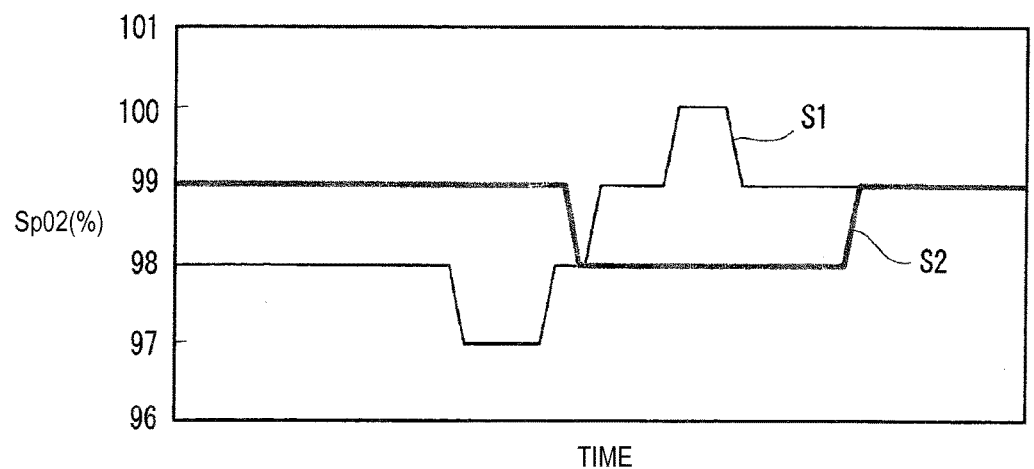
FIGS. 3A and 3B are views illustrating the operation of biological signal measuring apparatus of FIG. 2.

FIG. 3A shows the temporal changes of the first oxygen saturation S1 acquired by the first oxygen saturation acquiring section 23, and the second oxygen saturation S2 acquired by the second oxygen saturation acquiring section 24. As described above, the difference value |S1−S2| between the first oxygen saturation S1 and the second oxygen saturation S2 at certain timing can be used in determination of presence or absence of congenital heart disease in a neonate. When the values of S1 and S2 are changed every moment as shown in, for example, the middle portion of the graph, however, also the difference value |S1−S2| is changed every moment. Therefore, the medical person is puzzled to determine which value is employed.

Consequently, the first average oxygen saturation acquiring section 25 and the second average oxygen saturation acquiring section 26 average the values of the first oxygen saturation S1 and the second oxygen saturation S2 over a predetermined time period T to acquire the first average value A1 and the second average value A2. The temporal changes of the first average value A1 and the second average value A2 are moderate as compared to those of the first oxygen saturation S1 and the second oxygen saturation S2. Therefore, also the temporal change of the difference value |A1−A2| acquired by the difference value acquiring section 27 is moderate, and the medical person easily knows the value. The predetermined time period T is adequately determined so as to contain a plurality of periods when the first oxygen saturation S1 and the second oxygen saturation S2 are updated.

Figure 3B:
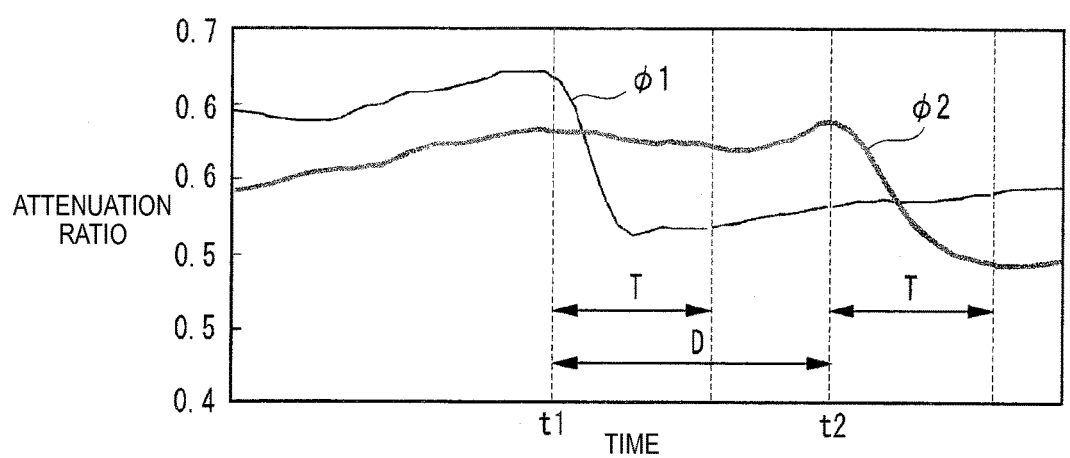

In a configuration where the first oxygen saturation S1 and the second oxygen saturation S2 are simply averaged and the difference value of the average values is acquired, however, another cause of a measurement error is produced. FIG. 3B shows the temporal changes of the first attenuation ratio φ1 acquired by the first attenuation ratio acquiring section 21, and the second attenuation ratio φ2 acquired by the second attenuation ratio acquiring section 22. The time period of arrival of blood from the heart to the first body portion is not equal to that of arrival of blood from the heart to the second body portion. Therefore, a time difference D is produced in the temporal changes of the first attenuation ratio φ1 and the second attenuation ratio φ2. In a significant comparison between the first oxygen saturation S1 and the second oxygen saturation S2, namely, it is required to consider the time difference.

Therefore, the first average oxygen saturation acquiring section 25 and the second average oxygen saturation acquiring section 26 acquire the first average value A1 and the second average value A2 of predetermined time periods T starting at different times t1 and t2, respectively. For example, the time t1 and the time t2 are determined so that the difference between the times corresponds to the time difference D. Therefore, the difference value |A1−A2| can be acquired based on the first oxygen saturation S1 and second oxygen saturation S2 of blood having the same meaning.

The difference value outputting section 28 outputs a signal indicating the difference value |A1−A2| acquired by the difference value acquiring section 27. As shown in FIG. 1, the biological signal measuring apparatus 2 includes a difference value displaying section 31. The a difference value displaying section 31 displays the difference value |A1−A2| (in the illustrated example, 7%) indicated by the signal which is output from the difference value outputting section 28.

According to the thus configured biological signal measuring system 1, the difference value between the arterial oxygen saturation in the first body portion of the subject, and that in the second body portion is displayed, and hence the medical person is not required to determine the difference value while visually comparing a plurality of arterial oxygen saturations with each other. The difference value is acquired based on the values of the arterial oxygen saturations which are averaged over the predetermined time periods T, respectively. Therefore, the temporal change can be moderated. Since the predetermined time periods start at the different times, it is possible to suppress a measurement error of the arterial oxygen saturation due to a difference between the time periods of arrival of blood from the heart to the first and second body portions. In congenital heart disease screening or the like, consequently, the burden of the medical person can be reduced, and correct determination can be supported.

As shown in FIG. 2, the biological signal measuring apparatus 2 may further include a cross-correlation function acquiring section 41. The cross-correlation function acquiring section 41 acquires a cross-correlation function of the temporal change of the first attenuation ratio φ1 acquired by the first attenuation ratio acquiring section 21, and that of the second attenuation ratio φ2 acquired by the second attenuation ratio acquiring section 22. The time t1 when the predetermined time period T for acquiring the first average value A1 by the first average oxygen saturation acquiring section 25 is started, and the time t2 when the predetermined time period T for acquiring the second average value A2 by the second average oxygen saturation acquiring section 26 is started are determined based on the cross-correlation function acquired by the cross-correlation function acquiring section 41. Specifically, when the times t1 and t2 are determined so that the cross-correlation function has the maximum value, the interval between the times t1 and t2 shown in FIG. 3B can be made coincident with the difference D between the time periods of arrival of blood from the heart to the first and second body portions.

The cross-correlation function acquiring section 41 may be configured so as to acquire a cross-correlation function of the temporal change of the first oxygen saturation S1 acquired by the first oxygen saturation acquiring section 23, and that of the second oxygen saturation S2 acquired by the second oxygen saturation acquiring section 24. Also in this case, when the times t1 and t2 are determined so that the cross-correlation function has the maximum value, the interval between the times t1 and t2 shown in FIG. 3B can be made coincident with the difference D between the time periods of arrival of blood from the heart to the first and second body portions.

According to the configuration, the predetermined time periods can be set in a portion in which the values related to the first and second body portions are similarly changed. Therefore, a measurement error of the arterial oxygen saturation due to a difference between the times of arrival of blood from the heart to the first and second body portions can be minimized. In congenital heart disease screening or the like, consequently, the burden of the medical person can be reduced, and correct determination can be supported.

As shown in FIGS. 1 and 2, the biological signal measuring apparatus 2 may further include a notifying section 42. The notifying section 42 is configured so as to, when the difference value |A1−A2| acquired by the difference value acquiring section 27 is equal to or larger than a predetermined threshold, take a given notifying state. For example, the threshold is set to 3% that is a value at which there is suspicion of congenital heart disease. In the case where the difference value |A1−A2| is equal to or larger than 3%, the notifying section 42 emits, for example, red light. In the case where the difference value is smaller than 3%, the notifying section 42 may emit light of a color other than red, or may be set to a non-light-emission state.

According to the configuration, the medical person can easily determine the condition of the subject by referring the state of the notifying section 42. In congenital heart disease screening or the like, consequently, the burden of the medical person can be reduced, and correct determination can be supported.

The notifying section 42 may be configured in the following manner. When the first average value A1 acquired by the first average oxygen saturation acquiring section 25 is smaller than a predetermined threshold, or when the second average value A2 acquired by the second average oxygen saturation acquiring section 26 is smaller than the threshold, the notifying section takes the given notifying state irrespective of the difference value |A1−A2| acquired by the difference value acquiring section 27. In this case, although not illustrated, the first average value A1 acquired by the first average oxygen saturation acquiring section 25, and the second average value A2 acquired by the second average oxygen saturation acquiring section 26 are directly input to the notifying section 42. For example, the threshold is set to 95% that is a value at which the condition of the subject is suspicious of not being normal. In the case where at least one of the first average value A1 and the second average value A2 is smaller than 95%, even when the difference value |A1−A2| is smaller than 3%, the notifying section 42 emits, for example, red light. In the case where both the first average value A1 and the second average value A2 are equal to or larger than 95%, and the difference value |A1−A2| is smaller than 3%, the notifying section 42 may emit light of a color other than red, or may be set to a non-light-emission state.

A reduction of the oxygen saturation indicates that the condition of the subject is not normal, and a countermeasure is required to be taken in advance of the determination of congenital heart disease in which the difference value is used. According to the configuration, the medical person can comprehensively know the abnormality of the subject through the notifying section 42, and take correctly and rapidly a countermeasure. In congenital heart disease screening or the like, consequently, the burden of the medical person can be reduced, and correct determination can be supported. Moreover, the notifying section 42 is single, and therefore the component cost can be suppressed.

As shown in FIG. 2, the biological signal measuring apparatus 2 may further include a first average value outputting section 43 and a second average value outputting section 44. The first average value outputting section 43 outputs a signal indicating the first average value A1 acquired by the first average oxygen saturation acquiring section 25. The second average value outputting section 44 outputs a signal indicating the second average value A2 acquired by the second average oxygen saturation acquiring section 26.

In this case, as shown in FIG. 1, the biological signal measuring apparatus 2 further includes a first average value displaying section 32 and a second average value displaying section 33. The first average value displaying section 32 displays the first average value A1 (in the illustrated example, 97%) indicated by the signal which is output from the first average value outputting section 43. The second average value displaying section 33 displays the second average value A2 (in the illustrated example, 90%) indicated by the signal which is output from the second average value outputting section 44.

According to the configuration, the medical person can check visually and individually the oxygen saturation in the first body portion, and that in the second body portion. A reduction of the oxygen saturation indicates that the condition of the subject is not normal, and a countermeasure is required to be taken in advance of the determination of congenital heart disease in which the difference value is used. According to the configuration, the medical person can comprehensively know the abnormality of the subject through the difference value displaying section 31, the first average value displaying section 32, and the second average value displaying section 33, and take correctly and rapidly a countermeasure. In congenital heart disease screening or the like, consequently, the burden of the medical person can be reduced, and correct determination can be supported.

As shown in FIG. 2, the biological signal measuring apparatus 2 may further include a heart rate acquiring section 45. The heart rate acquiring section 45 acquires the heart rate of the subject based on at least one of the first signal G1 which is output from the first optical sensor 3, and the second signal G2 which is output from the second optical sensor 4. Specifically, periodical changes of the first and second signals G1, G2 due to the blood pulsation owing to the heartbeat are detects, and determined as the heart rate of the subject.

In this case, as shown in FIG. 1, the biological signal measuring apparatus 2 further includes a single heart rate displaying section 34. The heart rate displaying section 34 displays the heart rate of the subject which is acquired by the heart rate acquiring section 45.

Unlike of the arterial oxygen saturation which is acquired in a plurality of body portions, the heart rate does not have a plurality of values at the same time. Although the heart rate can be acquired based on each of the first and second signals G1, G2, heart rates which are to be simultaneously displayed are unified into a single heart rate. Therefore, the medical person can know the heart rate without feeling cumbersome. In congenital heart disease screening or the like, consequently, the burden of the medical person can be reduced, and correct determination can be supported. Moreover, the heart rate displaying section 34 is single, and therefore the component cost can be suppressed.

For example, the heart rate acquiring section 45 selects one of the first signal G1 and the second signal G2 which contains a smaller amount of noises, and acquires the heart rate based on the selected one of the first signal G1 and the second signal G1. In this case, a more correct value can be provided as the heart rate of the subject.

Alternatively, the heart rate acquiring section 45 may be configured so as to acquire the average value of the heart rate based on the first signal G1, and the heart rate based on the second signal G2, as the heart rate. In this case, a more stable value can be provided as the heart rate of the subject.

Figure 4:
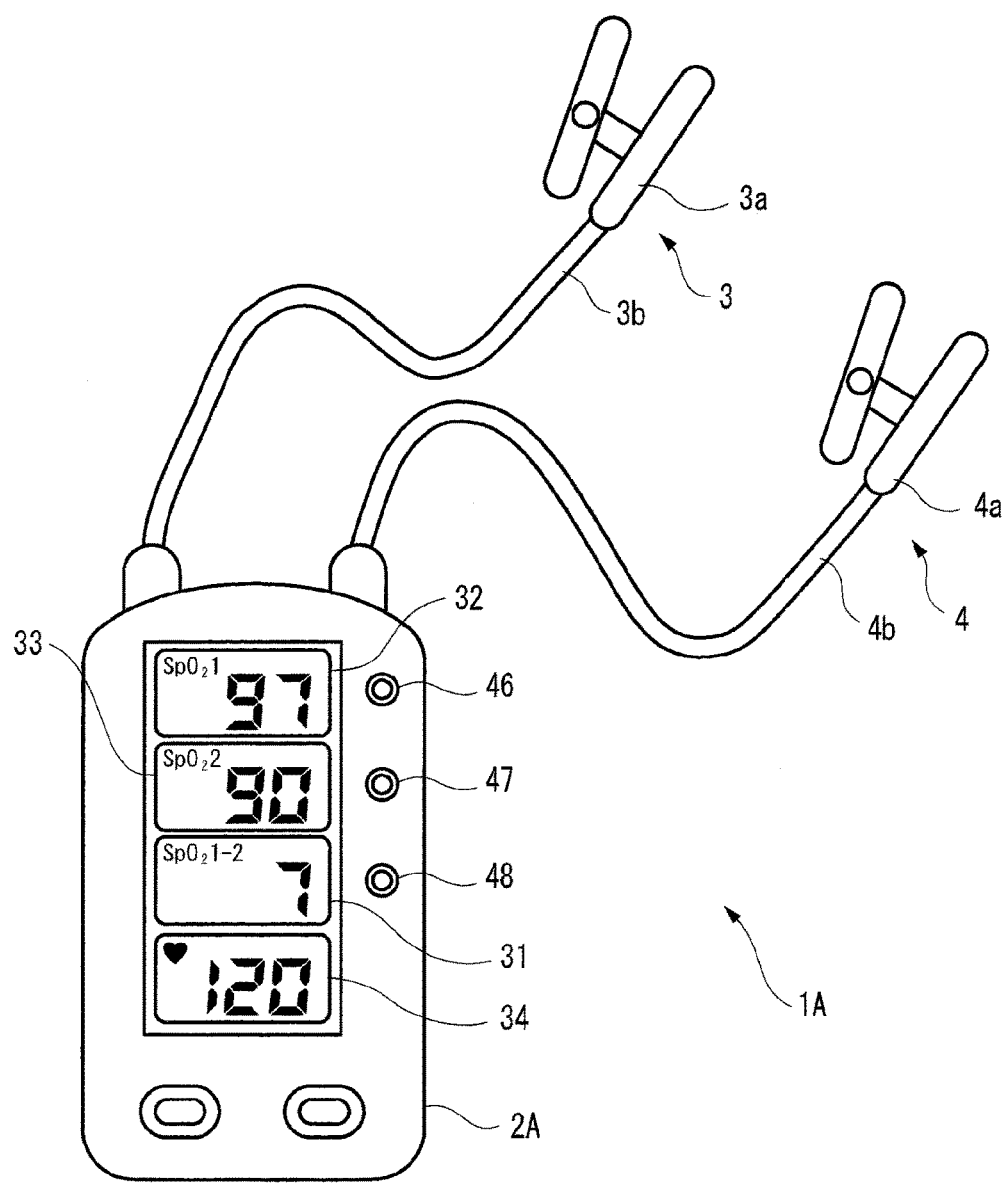
FIG. 4 is a view showing a biological signal measuring system of a second embodiment of the presently disclosed subject matter.
Figure 5:
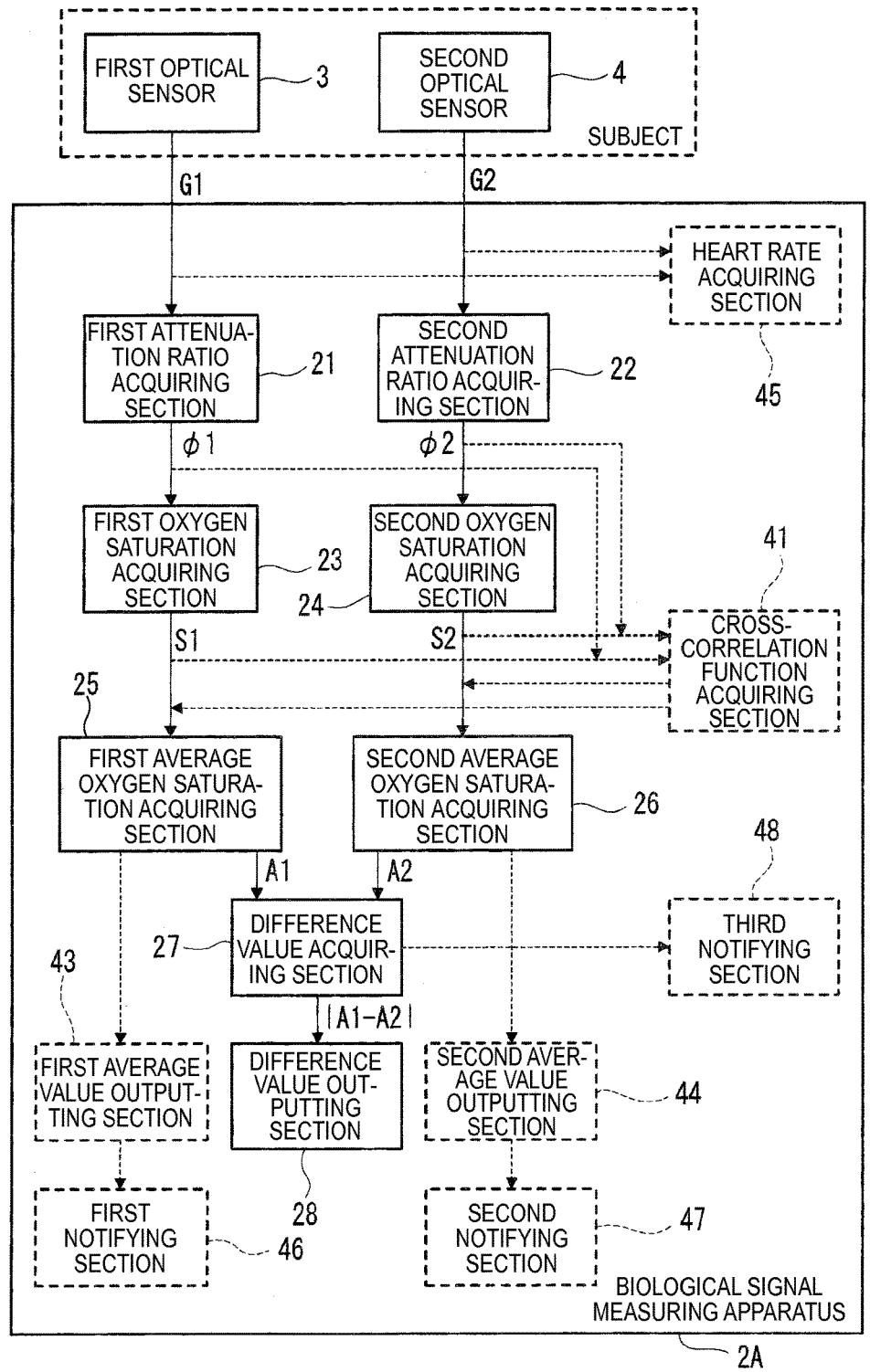
FIG. 5 is a functional block diagram showing the configuration of a biological signal measuring apparatus of the biological signal measuring system of FIG. 4.

Next, a biological signal measuring system 1A of a second embodiment of the presently disclosed subject matter will be described with reference to FIGS. 4 and 5. The components which are identical or similar to those of the biological signal measuring system 1 of the first embodiment are denoted by the same reference numerals, and repeated description is omitted.

The biological signal measuring system 1A includes a biological signal measuring apparatus 2A. The biological signal measuring apparatus 2A is different from the biological signal measuring apparatus 2 of the first embodiment in that the apparatus includes a first notifying section 46, a second notifying section 47, and a third notifying section 48, in place of the notifying section 42.

The first notifying section 46 is configured so as to, when the first average value A1 acquired by the first average oxygen saturation acquiring section 25 is smaller than a predetermined threshold, take a given notifying state. For example, the threshold is set to 95% that is a value at which the condition of the subject is suspicious of not being normal. In the case where the first average value A1 is smaller than 95%, the first notifying section 46 emits, for example, red light. In the case where the first average value A1 is equal to or larger than 95%, the first notifying section 46 may emit light of a color other than red, or may be set to a non-light-emission state.

The second notifying section 47 is configured so as to, when the second average value A2 acquired by the second average oxygen saturation acquiring section 26 is smaller than a predetermined threshold, take a given notifying state. For example, the threshold is set to 95% that is a value at which the condition of the subject is suspicious of not being normal. In the case where the second average value A2 is smaller than 95%, the second notifying section 47 emits, for example, red light. In the case where the second average value A2 is equal to or larger than 95%, the second notifying section 47 may emit light of a color other than red, or may be set to a non-light-emission state.

The third notifying section 48 is configured so as to, when the difference value |A1−A2| acquired by the difference value acquiring section 27 is equal to or larger than a predetermined threshold, take a given notifying state. For example, the threshold is set to 3% that is a value at which there is suspicion of congenital heart disease. In the case where the difference value |A1−A2| is equal to or larger than 3%, the third notifying section 48 emits, for example, red light. In the case where the difference value is smaller than 3%, the third notifying section 48 may emit light of a color other than red, or may be set to a non-light-emission state.

According to the configuration, it is possible to easily know whether each of the arterial oxygen saturation in the first body portion, that in the second body portion, and the difference value of the two arterial oxygen saturations is within the normal range or not. In the case where an abnormality occurs in the condition of the subject, furthermore, it is possible to easily identify which one of the measurement values causes the abnormality. In congenital heart disease screening or the like, consequently, the burden of the medical person can be reduced, and correct determination can be supported.

The embodiments have been described in order to facilitate understanding of the invention, and are not intended to limit the invention. It is a matter of course that the invention may be changed or improved without departing the spirit thereof, and includes equivalent of the embodiments.

In the embodiments, the signal which is output from the difference value outputting section 28, and which indicates the difference value |A1−A2| is used for displaying the difference value on the difference value displaying section 31. Alternatively, the signal output from the difference value outputting section 28 may be used for indicating the difference value by means of sounds, symbols, characters, or colors. This is applicable also to the first average value outputting section 43 and the second average value outputting section 44.

The difference value displaying section 31 is not always required to be disposed integrally with the biological signal measuring apparatus 2. The signal output from the difference value outputting section 28 may be transmitted by wired or wireless transmission, and the difference value may be displayed on a displaying device which is separately disposed. This is applicable also to the first average value displaying section 32 and the second average value displaying section 33.

In the embodiments, the difference value acquired by the difference value acquiring section 27 is used in determination of presence or absence of congenital heart disease in a neonate. The biological signal measuring system 1 (1A) of the presently disclosed subject matter can be used in an appropriate object in which the difference value can be set as a determination index. In this case, the threshold at which the notifying section 42 (third notifying section 48) takes the given notifying state can be adequately changed in accordance with the object.

According to an aspect of the presently disclosed subject matter, there is provided A biological signal measuring system comprising: a first optical sensor which is to be attached to a first body portion of a subject; a first attenuation ratio acquiring section which is configured to acquire a temporal change of a first attenuation ratio corresponding to an attenuation ratio of a plurality of wavelengths in the first body portion, based on a first signal output from the first optical sensor; a first oxygen saturation acquiring section which is configured to acquire a temporal change of a first oxygen saturation corresponding to an arterial oxygen saturation in the first body portion, based on the temporal change of the first attenuation ratio; a second optical sensor which is to be attached to a second body portion of the subject; a second attenuation ratio acquiring section which is configured to acquire a temporal change of a second attenuation ratio corresponding to an attenuation ratio of a plurality of wavelengths in the second body portion, based on a second signal output from the second optical sensor; a second oxygen saturation acquiring section which is configured to acquire a temporal change of a second oxygen saturation corresponding to an arterial oxygen saturation in the second body portion, based on the temporal change of the second attenuation ratio; a first average oxygen saturation acquiring section which is configured to acquire a first average value corresponding to an average value of the first oxygen saturation in a predetermined time period starting at a first time; a second average oxygen saturation acquiring section which is configured to acquire a second average value corresponding to an average value of the second oxygen saturation in the predetermined time period starting at a second time that is different from the first time; a difference value acquiring section which is configured to acquire a difference value between the first average value and the second average value; and a difference value displaying section which is configured to display the difference value.

According to the above configuration, a difference value of the arterial oxygen saturation in the first body portion of the subject, and that in the second body portion is displayed, and hence the medical person is not required to determine the difference value while visually comparing a plurality of arterial oxygen saturations with each other. The difference value is acquired based on the values of the arterial oxygen saturations which are averaged over the predetermined time periods T, respectively. Therefore, the temporal change can be moderated. Since the predetermined time periods start at the different times, it is possible to suppress a measurement error of the arterial oxygen saturation due to a difference between the time periods of arrival of blood from the heart to the first and second body portions. In congenital heart disease screening or the like, consequently, the burden of the medical person can be reduced, and correct determination can be supported.

The biological signal measuring system may further comprise: across-correlation function acquiring section which is configured to acquire a cross-correlation function of the temporal change of the first attenuation ratio and the temporal change of the second attenuation ratio, or a cross-correlation function of the temporal change of the first oxygen saturation and the temporal change of the second oxygen saturation, and the first time and the second time may be determined based on the cross-correlation function.

According to the above configuration, the predetermined time periods can be set in a portion in which the values related to the first and second body portions are similarly changed. Therefore, a measurement error of the arterial oxygen saturation due to a difference between the times of arrival of blood from the heart to the first and second body portions can be minimized. In congenital heart disease screening or the like, consequently, the burden of the medical person can be reduced, and correct determination can be supported.

The biological signal measuring system may further comprise: a notifying section which, when the difference value is equal to or larger than a threshold, is configured to take a given notifying state.

According to the above configuration, the medical person can easily determine the condition of the subject by referring the state of the notifying section. In congenital heart disease screening or the like, consequently, the burden of the medical person can be reduced, and correct determination can be supported.

When the first average value is smaller than a threshold, or when the second average value is smaller than the threshold, the notifying section may be configured to take the given notifying state irrespective of the difference value.

A reduction of the oxygen saturation indicates that the condition of the subject is not normal, and a countermeasure is required to be taken in advance of the determination of congenital heart disease in which the difference value is used. According to the above configuration, the medical person can comprehensively know the abnormality of the subject through the notifying section, and take correctly and rapidly a countermeasure. In congenital heart disease screening or the like, consequently, the burden of the medical person can be reduced, and correct determination can be supported. Moreover, the notifying section is single, and therefore the component cost can be suppressed.

The biological signal measuring system may further comprise: a first average value displaying section which is configured to display the first average value; and a second average value displaying section which is configured to display the second average value.

According to the above configuration, the medical person can check visually and individually the oxygen saturation in the first body portion, and that in the second body portion. A reduction of the oxygen saturation indicates that the condition of the subject is not normal, and a countermeasure is required to be taken in advance of the determination of congenital heart disease in which the difference value is used. According to the configuration, the medical person can comprehensively know the abnormality of the subject through the difference value displaying section, the first average value displaying section, and the second average value displaying section, and take correctly and rapidly a countermeasure. In congenital heart disease screening or the like, consequently, the burden of the medical person can be reduced, and correct determination can be supported.

The biological signal measuring system may further comprise: a first notifying section which, when the first average value is smaller than a threshold, is configured to take a given notifying state; a second notifying section which, when the second average value is smaller than a threshold, is configured to take a given notifying state; and a third notifying section which, when the difference value is equal to or larger than a threshold, is configured to take a given notifying state.

According to the above configuration, it is possible to easily know whether the arterial oxygen saturation in the first body portion, that in the second body portion, and the difference value of the two arterial oxygen saturations are in respective normal ranges or not. In the case where an abnormality occurs in the condition of the subject, furthermore, it is possible to easily identify which one of the measurement values causes the abnormality. In congenital heart disease screening or the like, consequently, the burden of the medical person can be reduced, and correct determination can be supported.

The biological signal measuring system may further comprise: a heart rate acquiring section which is configured to acquire a heart rate of the subject based on at least one of the first signal and the second signal; and a single heart rate displaying section which is configured to display the heart rate.

Unlike of the arterial oxygen saturation which is acquired in a plurality of body portions, the heart rate does not have a plurality of values at the same time. Although the heart rate can be acquired based on each of the first and second signals, heart rates which are to be simultaneously displayed are unified into a single heart rate. Therefore, the medical person can know the heart rate without feeling cumbersome. In congenital heart disease screening or the like, consequently, the burden of the medical person can be reduced, and correct determination can be supported. Moreover, the heart rate displaying section is single, and therefore the component cost can be suppressed.

The heart rate acquiring section may be configured to select one of the first signal and the second signal which contains a smaller amount of noises, and acquire the heart rate based on the selected one of the first signal and the second signal.

In this case, a more correct value can be provided as the heart rate of the subject.

The heart rate acquiring section may be configured to acquire, as the heart rate, an average value of: the heart rate based on the first signal; and the heart rate based on the second signal.

In this case, a more stable value can be provided as the heart rate of the subject.

What is claimed is:

1. A biological signal measuring system comprising:
 a first optical sensor which is to be attached to a first body portion of a subject;
 a first attenuation ratio acquiring section which is configured to acquire a temporally changing first attenuation ratio corresponding to an attenuation ratio of a plurality of wavelengths in the first body portion, based on a first signal output from the first optical sensor;
 a first oxygen saturation acquiring section which is configured to acquire a temporally changing first oxygen saturation corresponding to an arterial oxygen saturation in the first body portion, based on the temporally changing first attenuation ratio;
 a second optical sensor which is to be attached to a second body portion of the subject;
 a second attenuation ratio acquiring section which is configured to acquire a temporally changing second attenuation ratio corresponding to an attenuation ratio of a plurality of wavelengths in the second body portion, based on a second signal output from the second optical sensor;
 a second oxygen saturation acquiring section which is configured to acquire a temporally changing second oxygen saturation corresponding to an arterial oxygen saturation in the second body portion, based on the temporally changing second attenuation ratio;
 a first average oxygen saturation acquiring section which is configured to acquire a first average value corresponding to an average value of the first oxygen saturation in a predetermined time period starting at a first time;

a second average oxygen saturation acquiring section which is configured to acquire a second average value corresponding to an average value of the second oxygen saturation in the predetermined time period starting at a second time that is different from the first time;

a difference value acquiring section which is configured to acquire a difference value between the first average value and the second average value; and a difference value displaying section which is configured to display the difference value.

2. The biological signal measuring system according to claim 1, further comprising:

a cross-correlation function acquiring section which is configured to acquire a cross-correlation function of the temporally changing first attenuation ratio and the temporally changing second attenuation ratio, or a cross-correlation function of the temporally changing first oxygen saturation and the temporally changing second oxygen saturation, wherein the first time and the second time are determined based on the cross-correlation function.

3. The biological signal measuring system according to claim 1, further comprising: a notifying section which, when the difference value is equal to or larger than a threshold, is configured to take a given notifying state.

4. The biological signal measuring system according to claim 3, wherein, when the first average value is smaller than a threshold, or when the second average value is smaller than the threshold, the notifying section is configured to take the given notifying state irrespective of the difference value.

5. The biological signal measuring system according to claim 1, further comprising:

a first average value displaying section which is configured to display the first average value; and a second average value displaying section which is configured to display the second average value.

6. The biological signal measuring system according to claim 5, further comprising:

a first notifying section which, when the first average value is smaller than a threshold, is configured to take a given notifying state;

a second notifying section which, when the second average value is smaller than a threshold, is configured to take a given notifying state; and a third notifying section which, when the difference value is equal to or larger than a threshold, is configured to take a given notifying state.

7. The biological signal measuring system according to claim 1, further comprising:

a heart rate acquiring section which is configured to acquire a heart rate of the subject based on at least one of the first signal and the second signal; and a single heart rate displaying section which is configured to display the heart rate.

8. The biological signal measuring system according to claim 7, wherein the heart rate acquiring section is configured to select one of the first signal and the second signal which contains a smaller amount of noises, and acquire the heart rate based on the selected one of the first signal and the second signal.

9. The biological signal measuring system according to claim 7, wherein the heart rate acquiring section is configured to acquire, as the heart rate, and average value of: the heart rate based on the first signal and the heart rate based on the second signal.

* * * * *